US 010913956B2

(12) United States Patent
Passini et al.

(10) Patent No.: US 10,913,956 B2
(45) Date of Patent: Feb. 9, 2021

(54) GENE THERAPY FOR NEUROMETABOLIC DISORDERS (71) Applicant: Genzyme Corporation, Cambridge, MA (US)

(72) Inventors: Marco A. Passini, Northborough, MA (US); Greg Stewart, Plymouth, MN (US); James C. Dodge, Shrewsbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 15/201,268

(22) Filed: Jul. 1, 2016

(65) Prior Publication Data
US 2017/0152524 A1 Jun. 1, 2017

Related U.S. Application Data (63) Continuation of application No. 10/862,781, filed on Jun. 7, 2004, now abandoned, which is a continuation-in-part of application No. PCT/US2004/013685, filed on Apr. 30, 2004.

(60) Provisional application No. 60/475,726, filed on Jun. 4, 2003, provisional application No. 60/467,195, filed on May 1, 2003.

(51) Int. Cl.
A61K 48/00 (2006.01)
C12N 15/86 (2006.01)
A61K 38/46 (2006.01)
A61K 38/48 (2006.01)

(52) U.S. Cl.
CPC ............ *C12N 15/86* (2013.01); *A61K 38/465* (2013.01); *A61K 38/4886* (2013.01); *A61K 48/0075* (2013.01); *C12Y 301/04012* (2013.01); *A61K 48/00* (2013.01); *C12N 2750/14143* (2013.01)

(58) Field of Classification Search
CPC .......... C12N 15/86; C12N 2750/14143; C12Y 301/04012; A61K 48/0075; A61K 48/00
See application file for complete search history.

(56) References Cited

U.S. PATENT DOCUMENTS

| | | | | |
|---|---|---|---|---|
| 6,180,613 B1* | 1/2001 | Kaplitt | ................... | C07K 14/48 435/320.1 |
| 6,503,888 B1 | 1/2003 | Kaplitt et al. | | |
| 6,582,692 B1* | 6/2003 | Podsakoff | ............. | C12N 15/86 424/93.2 |
| 6,660,514 B1 | 12/2003 | Zolotukhin et al. | | |
| 7,090,836 B2 | 8/2006 | Desmaris et al. | | |
| 2003/0083299 A1 | 5/2003 | Ferguson | | |
| 2003/0118552 A1 | 6/2003 | Kaspar et al. | | |
| 2003/0165481 A1 | 9/2003 | Hersh | | |
| 2003/0228284 A1 | 12/2003 | McCown et al. | | |
| 2004/0258666 A1 | 12/2004 | Passini et al. | | |
| 2005/0271625 A1 | 12/2005 | Nash et al. | | |
| 2011/0263664 A1 | 10/2011 | Smith et al. | | |

FOREIGN PATENT DOCUMENTS

| | | |
|---|---|---|
| JP | 4979067 B2 | 7/2012 |
| WO | WO-01/36603 A2 | 5/2001 |
| WO | WO-2004/098648 A1 | 11/2004 |

OTHER PUBLICATIONS

Kaspar et al. Mol. Ther. 2002, 5:50-56.*
Bosch et al (Mol. Ther. Jan. 2000;1(1):63-70.*
Passini et al (Journal of Neuroscience Aug. 1, 2002;22(15):6437-46.*
Passini et al Society for Neuroscience Abstract Viewer and Itinerary Planner, vol. 2003, pp. Abstract No. 97.13, p. 1 (Year: 203).*
Passini et al Molecular Therapy, 11,754-762 (Year: 2005).*
Suzuki et al Acta Pediatr. Suppl. 443, 54-62 (Year: 2003).*
Walkley et al ,(Brain Pathol. 8(1):175-93 (Year: 1998).*
Wang et al. J. Neurosci. 22(16):6920-6928 (Year: 2002).*
Kaspar et al. Mol. Ther. 5(1): 50-56 (Year: 2002).*
Adalbert, R. et al. (Apr. 2007). "Abeta, Tau and ApoE4 in Alzheimer's Disease: The Axonal Connection," *Trends Mol Med.* 13(4):135-42.
Barranger, J.A. et al. (1999). "Geme Transfer Approaches to the LYsosomal Storage Disorgers," *Neurochemical Research* 24(4):601-615.
Beutler, E. et al. (1995). *In the Metabolic and Molecular Bases of Inherited Disease*, Scriver C.R. (ed.), McGraw Hill, New York, vol. II. 7$^{th}$ ed: Gaucher Disease, pp. 2641-2670.
Bosch, A. et al. (Jan. 2000). "Long-Tern and Significant Correction of Brain Lesions in Adult Mucopolysaccharidosis Type VII Mice Using Recombinant AAV Vectors," *Molecular Therapy* 1(1):63-70.
Brooks, A.L. et al. (Apr. 30, 2002). "Functional Correction of Established Central Nervous System Deficits in an Animal Model of Lysosomal Storage Disease with Feline Immunodeficiency Virus-based Vectors," *Proc Natl Acad Sci USA* 99:6216-6221.
Burger, C. et al. (Aug. 2004). "Recombinant AAV Viral Vectors Pseudotyped with Viral Capsids from Serotypes 1, 2, and 5 Display Differential Efficiency and Cell Tropism After Delivery to Different Regions of the Central Nervous System," *Mol. Ther.* 10, 302-317.
Carter, J.E. et al. (May 2001). "Gene Therapy for Neurodegenerative Diseases: Fact or Fiction?" *British Journal of Psychiatric* 178:392-394.

(Continued)

*Primary Examiner* — Anoop K Singh
(74) *Attorney, Agent, or Firm* — Morrison & Foerster LLP (57) ABSTRACT

The disclosure pertains to methods and compositions for treating disorders affecting the central nervous system (CNS). These disorders include neurometabolic disorders such as lysosomal storage diseases that affect the central nervous system, e.g., Niemann-Pick A disease. They also include disorders such as Alzheimer's disease. The disclosed methods involve contacting an axonal ending of a neuron with a composition containing high titer AAV carrying a therapeutic transgene so that the AAV vector is axonally transported in a retrograde fashion and transgene product is expressed distally to the administration site.

4 Claims, 6 Drawing Sheets

(56) References Cited

OTHER PUBLICATIONS

Chamberlin, N.L. et al. "Recombinant Adeno-Virus Vector use for Transgene Expression and Anterograde Tract Tracing in the CNS," *Brain Research* 793:169-175 (1998).

Datto, J. et al. (2002). "Distribution of AAV-1 GFP with Respect to Time, Distance Traveled, and Expression Following Injection to the Midbrain Program No. 623.4," Abstract, *presented at the Society for Neuroscience*, Washington D.C., located at <http://sfn.scholarone.com/itin2002/main.html?new_page_id=126&abstract_id12481&p_nu...> last visited on Aug. 15, 2006, one page.

Davidson, B.L. et al. (May 2003). "Viral Vectors for Gene Delivery to the Nervous System," *Nature* 4:355-364.

Davidson, B.L. et al. (Mar. 2000). "Recombinant Adeno-Associated Virus Type 2, 4, and 5 vectors: Transduction of Variant Cell Types and Regions in the Mammalian Central Nervous System," *PNAS* 97(7):3428-3432.

Dodge, J.C. et al. (Dec. 6, 2005). "Gene Transfer of Human Acid Sphingomyelinase Corrects Neuropathology and Motor Deficits in a Mouse Model of Niemann-Pick Type A Disease," *Proc Nat Acad Sci USA*. 102(49): 17822-17827.

Elliger, S.S. et al. (Jun. 1999). "Elimination of Lysosomal Storage in Brains of MPS VII Mice Treated by Intrathecal Administration of an Adeno-Associated Virus Vector," *Gene Therapy* 6(6):1175-1178.

Frisella, W.A. et al. (Mar. 2001). "Intracranial Injection of Recombinant Adeno-associated Virus Improves Cognitive Function in a Minute Model of Mucopolysaccharidosis Type VII," *Molecular Therapy* 3(3):351-358.

Gao, G.P. et al. (Sep. 3, 2002). "Novel Adeno-Associated Viruses From Rhesus Monkeys as Vectors for Human Gene Therapy," *Proc. Nat. Acad. Sci.* 99(18):11854-11859.

Ghodsi, A. et al. (Nov. 1, 1998). "Extensive Beta-glucuronidase Activity in Murine Central Nervous System After Adenovirus-mediated Gene Transfer to Brain," *Hum Gene Ther* 9: 2331-2340.

Goncalves, M.A.F.V. et al. (2005). "Adeno-Associated Virus: From Defective Virus to Effective Vector," *Virology Journal* 2(43):1-17.

Haskell, R.E. et al. (Jan. 2003). "Viral-mediated Delivery of the Late-Infantile Neuronal Ceroid Lipofuscinosis Gene, TPP-I to the Mouse Central Nervous System," *Gene Ther.* 10(1):34-42.

Hsich, G. et al. (Mar. 20, 2002). "Critical Issues in Gene Therapy for Neurologic Disease," *Hum. Gene Ther.* 13: 579-604.

Ioannou, Y.A. et al. (2003). "Gene therapy for lysosomal storage disorders," *Expert Opinion in Biology and Therapy* 3(5):789-801.

J.G. Hardman, et al., ed. (1996) *Goodman & Gilman's the Pharmacological Basis of Therapeutics*, McGraw-Hill, New York, NY., pp. 77-101, 30 pages.

Jin, H.K. and Schuchman, E.H. (Dec. 2003). "Ex Vivo Gene Therapy Using Bone Marrow-Derived Cells: Combined Effects of Intracerebral and intravenous Transplantation in a Mouse Model of Nieman-Pick Disease," *Molecular Therapy* 8(6):876-885.

Jin, H.K. et al. (2002). "Intracerebral Transplantation of Mesenchymal Stem Cells into Acid Sphingomyelinase-Deficient Mice Delays the Onset of Neurological Abnormalities and Extends Their Life Span," *Journal of Clinical Investigation* 109:1183-1191.

Kaemmerer, W.F. et al. (Nov. 2000). "In Vivo Transduction of Cerebellar Purkinje Cells Using Adeno-Associated Virus Vectors," *Mol Ther.* 2(5):446-57.

Kaiser, J. (Aug. 3, 2007). "Clinical research. Death prompts a review of gene therapy vector," *Science* 317(5838):580.

Kaplitt, M.G. et al. (Oct. 1994). "Long-Term Gene Expression and Phenotypic Correction Using Adeno-Associated Virus Vectors in the Mammalian Brain," *Nature Genetics* 8:148-154.

Kaspar, Bk. et al. (Jan. 2002). "Targeted Retrograde Gene Delivery for Neuronal Protection," *Mol Ther.* 5(1): 50-56.

Kaspar, B.K. et al. (Aug. 2003). "Retrograde Viral Delivery of IGF-1 Prolongs Survival in a Mouse ALS Model," *Science* 301:829-842.

Koeberl, D.D. et al. (Mar. 2006). "Age-Related Efficacy with an AAV Vector in Fabry Disease Mice," *Molecular Genetics and Metabolism* 96(3): 83-84.

Liu, Y. et al. High level of transduction of mammalian brain by adeno-associated type 1 virus vector. Society for Neuroscience Abstract Viewer, 2002. Online. Program No. 902.2.

Marr, R.A. et al. (Mar. 15, 2003). "Neprilysin Gene Transfer Reduces Human Amyloid Pathology in Transgenic Mice," *The Journal of Neuroscience* 23(6): 1992-1996.

Matalon, R. et al. (May 2003). "Adeno-Associated Virus-Mediated Aspartoacylase Gene Transfer to the Brain of Knockout Mouse for Canavan Disease," *Mol Ther.* 7(5 pt 1):580-587.

Meikle, P.J. et al. (1999). "Prevalence of Lysosomal Storage Disorders," *JAMA* 281:249-254.

Miranda, S.R. et al. (Oct. 2000). "Hematoppoietic Stem Cell Gene Therapy Leads to Marked Visceral Organ Improvements and a Delayed Onset of Neurological Abromalities in the Acid Sphingomyekubase Deficient Mouse Model of Neimann-Pick Disease," *Gene Therapy* 7(20):1768-1776.

Passini, M.A. et al. (Dec. 2001). "Widespread Gene Delivery and Structure-Specific Patterns of Expression in the Brain After Intraventricular Injections of Neonatal Mice with an Adeno-Associated Virus Vector," *Journal of Virology* p. 12382-12392.

Passini, M.A. et al. (Aug. 1, 2002). "Distribution of a Lysosomal Enzyme in the Adult Brain by Axonal Transport and by Cells of the Rostral Migratory Stream," *The Journal of Neuroscience* 22(15):6437-6446.

Passini, M.S. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of B-Glucuronidase-Deficient Mice," *Journal of Virology* p. 7034-7040.

Schuchman, E.H. (Nov. 1999). "Hematopoietic Stem Cell Gene Therapy for Niemann-Pick Disease and Other Lysosomal Storage Diseases," *Chemistry and Physics of Lipds* 102: 179-188.

Sferra, T.J. et al. (Mar. 2000). "Recombinant Adeno-Associated Virus-Mediated Correction of Lysosomal Storage within the Central Nervous System of the Adult Mycopolysaccharidosis Type VII Mouse," *Human Gene Therapy* 11:507-519.

Shevtsova, Z. et al.( 2005) "Promoters and Serotypes: Targeting of Adeno-Associated Virus Vectors for Gene Transfer in the Rat Central Nervous System in Vitro and in Vivo," *Exp Physiol* 90(1)53-59.

Skorupa, A.F. et al. (1999). "Sustained Production of B-Glucuronidase from Localized Sites after AAV Vector Gene Transfer Results in Widespread Distribution of Enzyme and Reversal of Lysosomal Storage Lesions in a Large Volume of Brain in Mucopolysaccharidosis VII Mice," *Experimental Neurology* 160: 17-27.

Stein, C.S.et al. (Apr. 1999). "Systemic and Central Nervous System Correction of Lysosomal Storage in Mucopolysaccaridosis Type VII Mice," *Journal of Virology* 73(4):3424-3428.

Suchi, M. et al. (Apr. 1992). "Retroviral-Mediated Transfer of the Human Acid Sphigomyelinase cDNA: Correction of the Metabolic Defect in Cultured Niemann-Pick Disease Cells," *Proc. Nat. Acad. Sci.* 89:3227-3231.

Suzuki et al. Acta Pediatr. Suppl. 443:54-62.

Vite, C.H. et al. (2003)."Adeno-Associated Virus Vector-Mediated Transduction in the Cat Brain", *Gene Therapy* 10: 1874-1881.

Walkley, S.U. (Jan. 1998). "Cellular Pathology of Lysosomal Storage Disorders," *Brain Pathol* .8(1): 175-93.

Wang, L.J. et al. (Aug. 15, 2002). "Neuroprotective Effects of Glial Cell Line-Derived Neurotrophic Factor Mediated by an Adeno-Associated Virus Vector in a Transgenic Animal Model of Amyotrophic Lateral Sclerosis," *J. Neurosci.* 22(16): 6920-6928.

Wang, C. et al. (2003). "Recombinant AAV Serotype 1 Transduction Efficiency and Tropism in the Murine Brain," *Gene Therapy* 10:1528-1537.

Xiao, X. et al. (1997). "Gene Transfer by Adeno-Associated Virus Vectors into the Central Nervous System," *Experimental Neurology* 144:113-124.

Yasojima, K. et al. (Apr. 1992). "Reduced Neprilysin in High Plaque Areas of Alzheimer Brian: A Possible Relationship to Deficient Degradation of β-Amyloid Peptide," *Neuroscience Letters* 297(2):97-100.

(56) References Cited

OTHER PUBLICATIONS

Iwata, N. et al. (Jan. 28, 2004). "Presynaptic Localization of Neprilysin Contributes to Efficient Clearance of Arnyloid-β Peptide in Mouse Brain," *Journal of Neuroscience* 24(4):991-998.

Vogler, C. et al. (Jul.-Aug. 2005, e-pub. Oct. 12, 2005). "Early Onset of Lysosomal Storage Disease in a Murine Model of Mucopolysaccharidosis Type VII: Undegraded Substrate Accumulates in Many Tissues in the Fetus and Very Young MPS VII Mouse," *Pediatr Dev Pathol* 8(4):453-462.

\* cited by examiner

GENE THERAPY FOR NEUROMETABOLIC DISORDERS

CROSS-REFERENCE TO RELATED APPLICATIONS

This application is a continuation of U.S. patent application Ser. No. 10/862,781, filed on Jun. 7, 2004, which is a continuation in part of PCT application No. 04/13685 filed on Apr. 30, 2004, which claims priority to U.S. patent application No. 60/467,195 filed on May 1, 2003 and U.S. patent application No. 60/475,726 filed on Jun. 4, 2003, herein incorporated by reference in their entirety.

FIELD OF THE INVENTION

The present invention relates to compositions and methods for treating disorders affecting the central nervous system (CNS). The invention further relates to compositions comprising viral vectors such as adeno-associated virus (AAV) vectors, and methods of administration thereof.

BACKGROUND OF THE INVENTION

A group of metabolic disorders known as lysosomal storage diseases (LSD) includes over forty genetic disorders, many of which involve genetic defects in various lysosomal hydrolases. Representative lysosomal storage diseases and the associated defective enzymes are listed in Table 1.

TABLE 1

| Lysosomal storage disease | Defective enzyme |
|---|---|
| Aspartylglucosaminuria | Aspartylglucosaminidase |
| Fabry | α-Galactosidase A |
| Infantile Batten Disease* (CNL1) | Palmitoyl Protein Thioesterase |
| Classic Late Infantile Batten Disease* (CNL2) | Tripeptidyl Peptidase |
| Juvenile Batten Disease* (CNL3) | Lysosomal Transmembrane Protein |
| Batten, other forms* (CNL4-CNL8) | Multiple gene products |
| Cystinosis | Cysteine transporter |
| Farber | Acid ceramidase |
| Fucosidosis | Acid α-L-fucosidase |
| Galactosidosialidosis | Protective protein/cathepsin A |
| Gaucher types 1, 2*, and 3* | Acid β-glucosidase, or glucocerebrosidase |
| $G_{M1}$ gangliosidosis* | Acid β-galactosidase |
| Hunter* | Iduronate-2-sulfatase |
| Hurler-Scheie* | α-L-Iduronidase |
| Krabbe* | Galactocerebrosidase |
| α-Mannosidosis* | Acid α-mannosidase |
| β-Mannosidosis* | Acid β-mannosidase |
| Maroteaux-Lamy | Arylsulfatase B |
| Metachromatic leukodystrophy* | Arylsulfatase A |
| Morquio A | N-Acetylgalactosamine-6-sulfate sulfatase |
| Morquio B | Acid β-galactosidase |
| Mucolipidosis II/III* | N-Acetylglucosamine-1-phosphotransferase |
| Niemann-Pick A*, B | Acid sphingomyelinase |
| Niemann-Pick C* | NPC-1 |
| Pompe* | Acid α-glucosidase |
| Sandhoff* | β-Hexosaminidase B |
| Sanfilippo A* | Heparan N-sulfatase |
| Sanfilippo B* | α-N-Acetylglucosaminidase |
| Sanfilippo C* | Acetyl-CoA:α-glucosaminide N-acetyltransferase |
| Sanfilippo D* | N-Acetylglucosamine-6-sulfate sulfatase |
| Schindler Disease* | α-N-Acetylgalactosaminidase |
| Schindler-Kanzaki | α-N-Acetylgalactosaminidase |

TABLE 1-continued

| Lysosomal storage disease | Defective enzyme |
|---|---|
| Sialidosis | α-Neuramidase |
| Sly* | β-Glucuronidase |
| Tay-Sachs* | β-Hexosaminidase A |
| Wolman* | Acid Lipase |

*CNS involvement

The hallmark feature of LSD is the abnormal accumulation of metabolites in the lysosomes which leads to the formation of large numbers of distended lysosomes in the perikaryon. A major challenge to treating LSD (as opposed to treating a liver-specific enzymopathy) is the need to reverse lysosomal storage pathology in multiple separate tissues. Some LSDs can be effectively treated by intravenous infusion of the missing enzyme, known as enzyme replacement therapy (ERT). For example, Gaucher type 1 patients have only visceral disease and respond favorably to ERT with recombinant glucocerebrosidase (Cerezyme®, Genzyme Corp.). However, patients with metabolic disease that affects the CNS (e.g., type 2 or 3 Gaucher disease) do not respond to intravenous ERT because the replacement enzyme is prevented from entering the brain by the blood brain barrier (BBB). Furthermore, attempts to introduce a replacement enzyme into the brain by direct injection have been unsuccessful in part due to enzyme cytotoxicity at high local concentrations (unpublished observations) and limited parenchymal diffusion rates in the brain (Pardridge, Peptide Drug Delivery to the Brain, Raven Press, 1991).

Alzheimer's disease (AD) is a disorder affecting the central nervous system (CNS) characterized by the accumulation of amyloid β-peptide (Aβ) due to decreased Aβ catabolism. As Aβ accumulates, it aggregates into extracellular plaques, causing impairment of synaptic function and loss of neurons. The pathology leads to dementia, loss of coordination, and death.

Gene therapy is an emerging treatment modality for disorders affecting the CNS, including LSDs and Alzheimer's disease. In this approach, restoration of the normal metabolic pathway and reversal of pathology occurs by transducing affected cells with a vector carrying a healthy version or a modified version of the gene.

CNS gene therapy has been facilitated by the development of viral vectors capable of effectively infecting post-mitotic neurons. For a review of viral vectors for gene delivery to the CNS, see Davidson et al. (2003) Nature Rev., 4:353-364. Adeno-associated virus (AAV) vectors are considered optimal for CNS gene therapy because they are substantially non-toxic, non-immunogenic, neurotropic and can sustain long-term expression in the CNS (Kaplitt et al. (1994) Nat. Genet., 8:148-154; Bartlett et al. (1998) Hum. Gene Ther., 9:1181-1186; and Passini et al. (2002) J. Neurosci., 22:6437-6446).

A therapeutic transgene product, e.g., an enzyme, can be secreted by transduced cells and subsequently taken up by other cells, in which it then alleviates pathology. This process is known as cross-correction (Neufeld et al. (1970) Science, 169:141-146). However, the correction of pathology, such as storage pathology in the context of LSD, is typically confined to the immediate vicinity of the injection site because of limited parenchymal diffusion of the injected vector and the secreted transgene product (Taylor et al. (1997) Nat. Med., 3:771-774; Skorupa et al. (1999) Exp. Neurol., 160:17-27). Thus, neuropathology affecting multiple brain regions requires widespread vector delivery, using multiple spatially distributed injections, especially in a large brain such as human. This significantly increases the risk of brain damage. In addition, some regions of the brain may be difficult to access surgically. Thus, other modes of vector transport within the CNS, besides diffusion, would be beneficial.

When administered at axonal endings, some viruses are internalized and transported retrogradely along the axon to the nucleus. Neurons in one brain region are interconnected by axons to distal brain regions thereby providing a transport system for vector delivery. Studies with adenovirus, HSV, and pseudo-rabies virus have utilized trafficking properties of these viruses to deliver genes to distal structures within the brain (Soudas et al. (2001) FASEB J., 15:2283-2285; Breakefield et al. (1991) New Biol., 3:203-218; and deFalco et al. (2001) Science, 291:2608-2613). However, drawbacks associated with these viral vectors, e.g., immunogenicity and/or cell toxicity, limit their utility.

Several groups have reported that the transduction of the brain by AAV serotype 2 (AAV2) is limited to the intracardial injection site (Kaplitt et al. (1994) Nat. Genet., 8:148-154; Passini et al. (2002) J. Neurosci., 22:6437-6446; and Chamberlin et al. (1998) Brain Res., 793:169-175). One recent report suggests that retrograde axonal transport of AAV2 can also occur in select circuits of the normal rat brain (Kaspar et al. (2002) Mol. Ther., 5:50-56). However, it is not known what specific parameters were responsible for the observed axonal transport, and whether sufficient and effective axonal transport would occur in a diseased neuron that is in a state of cellular dysfunction. Indeed, lesions observed in LSD neurons have been reported to interfere with or even block axonal transport (reviewed in Walkley (1998) Brain Pathol., 8:175-193), suggesting that disease-compromised neurons would not support trafficking of AAV along their axons.

Therefore, there is a need in the art to develop new therapeutic methods for treating metabolic disorders that affect the CNS.

SUMMARY OF THE INVENTION

The invention provides methods and compositions for treating or preventing metabolic disorders, such as lysosomal storage diseases (LSD) that are characterized by or associated with a risk of diminution of CNS function.

The invention provides methods and compositions for treating or preventing disorders affecting the central nervous system (CNS), such as Alzheimer's disease that are characterized by or associated with a risk of diminution of CNS function.

The invention further provides methods for minimally invasive targeted delivery of a transgene to select regions in the brain of an affected subject.

Additional advantages of the invention will be set forth in part in the following description, and in part will be understood from the description, or may be learned by practice of the invention.

Acid sphingomyelinase (ASM) knockout mice, a model of Niemann-Pick Type A disease, were administered an AAV2 vector carrying the human ASM gene (AAV-ASM) by a single intracranial injection into one hemisphere of the brain. The present invention is based, in part, on the discovery and demonstration that the injection of high titer AAV-ASM into the diseased brain results in AAV-ASM expression within multiple distal sites in a pattern consistent with the topographical organization of the projection neurons that innervate the injection site. The invention is further based, in part, on the discovery and demonstration of extensive correction of lysosomal storage pathology at the injection site and distal sites to which AAV-ASM was transported and where ASM was expressed.

Accordingly, in one aspect, the present invention provides methods for treating neurometabolic disorders in mammals. The populations treated by the methods of the invention include, but are not limited to, patients having or at risk for developing a LSD, such as disorders listed in Table 1, particularly, if such disease affects the CNS. In an illustrative embodiment, the disease is Niemann-Pick A disease.

In one aspect, the disclosed methods include administering to the CNS of an afflicted subject an AAV viral vector carrying a transgene encoding a therapeutic product and allowing the transgene to be expressed within the CNS distally from the administration site at a therapeutic level. In addition, the vector may comprise a polynucleotide encoding for a biologically active molecule effective to treat the CNS disorder. Such biologically active molecules may comprise peptides including but not limited to native or mutated versions of full-length proteins, native or mutated versions of protein fragments, synthetic polypeptides, antibodies, and antibody fragments such as Fab' molecules. Biologically active molecules may also comprise nucleotides including single-stranded or double-stranded DNA polynucleotides and single-stranded or double-stranded RNA polynucleotides. For a review of exemplary nucleotide technologies that may be used in the practice of the methods disclosed herein, see Kurreck, (2003) J., Eur. J. Biochem. 270, 1628-1644 [antisense technologies]; Yu et al., (2002) PNAS 99(9), 6047-6052 [RNA interference technologies]; and Elbashir et al., (2001) Genes Dev., 15(2):188-200 [siRNA technology].

In an illustrative embodiment, the administration is accomplished by direct intraparenchymal injection of a high titer AAV vector solution into the diseased brain. Thereafter the transgene is expressed distally, contralaterally or ipsilaterally, to the administration site at a therapeutic level at least 2, 3, 5, 8, 10, 15, 20, 25, 30, 35, 40, 45, or 50 mm from the administration site.

In another aspect, the invention also provides a method of delivering a recombinant AAV genome to the nucleus of a disease-compromised neuron in vivo. In some embodiments, the cellular pathology exhibited by the neuron is that of a lysosomal storage disease such as disorders listed in Table 1. In an illustrative embodiment, the disease is Niemann-Pick A disease. In other embodiments, the cellular pathology exhibited is that of Alzheimer's disease. The method of delivering a recombinant AAV genome to the nucleus of a disease-compromised neuron comprises contacting an axonal ending of the disease-compromised neuron with a composition comprising an AAV viral particle comprising the recombinant AAV genome and allowing the viral particle to be endocytosed and retrogradely transported intracellularly along the axon to the nucleus of the neuron. The concentration of the vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml). In certain embodiments, the neuron is a projection neuron and/or the distance of the axonal ending to the nucleus of the neuron is at least 2, 3, 5, 8, 10, 15, 20, 25, 30, 35, 40, 45, or 50 mm.

In another aspect, the invention provides a method of delivering a therapeutic transgene product to a target cell of the CNS, which is a neuron or a glial cell, in a mammal afflicted with a neurometabolic disorder, e.g., an LSD that affects the CNS. The method includes contacting an axonal ending of a neuron with a composition containing an AAV vector carrying at least a part of a gene encoding a therapeutic transgene product, allowing the viral particle to be endocytosed and retrogradely transported intracellularly along the axon to the nucleus of the neuron; allowing the therapeutic transgene product to be expressed and secreted by the neuron, and allowing the target cell to uptake the therapeutic transgene product, wherein the therapeutic transgene product thereby alleviates pathology in the target cell. In certain embodiments, the concentration of the vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml).

In the methods of the invention, the therapeutic transgene encodes a biologically active molecule, expression of which in the CNS results in at least partial correction of neuropathology. In some embodiments, the therapeutic transgene product is a lysosomal hydrolase. In an illustrative embodiment, the lysosomal hydrolase is ASM. In other embodiments, the therapeutic transgene is a metalloendopeptidase, e.g., neprilysin.

It is to be understood that both the foregoing general description and the following detailed description are exemplary and explanatory only and are not restrictive of the invention as claimed.

BRIEF DESCRIPTION OF THE FIGURES

FIG. 1C is a schematic diagram showing the connections of the intrahippocampal and entorhinodentate circuits of the mouse brain. Injection into the hippocampus (10) results in infection and transduction of cell bodies located in the cornu ammonis area 3 (CA3) and in the dentate granule cell layer (G). In addition, a subset of the injected AAV vector infects the axonal endings of the projection neurons innervating the injection site, undergoes retrograde axonal transport, and delivers the transgene to the CA3 field (CA3) and hilus (H) in the contralateral part of the hippocampus (20), and ipsilaterally in the entorhinal cortex (30).

FIG. 2C is a schematic diagram showing the connections of the septohippocampal circuit. Injection into the hippocampus resulted in transduction to cell bodies located in the CA3 field (11). In addition, a subset of the AAV vector infects the axonal endings of the projection neurons innervating the injection site, undergoes retrograde axonal transport, and delivers the transgene to the medial septum (40).

DETAILED DESCRIPTION OF THE INVENTION

In order that the present invention may be more readily understood, certain terms are first defined. Additional definitions are set forth throughout the detailed description.

The term "transgene" refers to a polynucleotide that is introduced into a cell of and is capable of being translated and/or expressed under appropriate conditions and confers a desired property to a cell into which it was introduced, or otherwise leads to a desired therapeutic outcome.

The terms "genome particles (gp)," or "genome equivalents," as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

The terms "therapeutic," "therapeutically effective amount," and their cognates refer to that amount of a compound that results in prevention or delay of onset or amelioration of symptoms of in a subject or an attainment of a desired biological outcome, such as correction of neuropathology, e.g., cellular pathology associated with a lysosomal storage disease such as that described herein or in Walkley (1998) Brain Pathol., 8:175-193. The term "therapeutic correction" refers to that degree of correction that results in prevention or delay of onset or amelioration of symptoms in a subject. The effective amount can be determined by methods well-known in the art and as described in the subsequent sections.

Methods and Compositions

ASMKO mice are an accepted model of types A and B Niemann-Pick disease (Horinouchi et al. (1995) Nat. Genetics, 10:288-293; Jin et al. (2002) J. Clin. Invest., 109:1183-1191; and Otterbach (1995) Cell, 81:1053-1061). Niemann-Pick disease (NPD) is classified as a lysosomal storage disease and is an inherited neurometabolic disorder characterized by a genetic deficiency in acid sphingomyelinase (ASM; sphingomyelin cholinephosphohydrolase, EC 3.1.3.12). The lack of functional ASM protein results in the accumulation of sphingomyelin substrate within the lysosomes of neurons and glia throughout the brain. This leads to the formation of large numbers of distended lysosomes in the perikaryon, which are a hallmark feature and the primary cellular phenotype of type A NPD. The presence of distended lysosomes correlates with the loss of normal cellular function and a progressive neurodegenerative course that leads to death of the affected individual in early childhood (The Metabolic and Molecular Bases of Inherited Diseases, eds. Scriver et al., McGraw-Hill, New York, 2001, pp. 3589-3610). Secondary cellular phenotypes (e.g., additional metabolic abnormalities) are also associated with this disease, notably the high level accumulation of cholesterol in the lysosomal compartment. Sphingomyelin has strong affinity for cholesterol, which results in the sequestering of large amounts of cholesterol in the lysosomes of ASMKO mice and human patients (Leventhal et al. (2001) J. Biol. Chem., 276:44976-44983; Slotte (1997) Subcell. Biochem., 28:277-293; and Viana et la. (1990) J. Med. Genet., 27:499-504.)

The present invention is based, in part, on the discovery and demonstration that an intrahippocampal injection of high titer AAV-ASM into the diseased brains of ASMKO mice results in expression of ASM mRNA and protein distally from the injection site in a pattern consistent with the topographical organization of the projection neurons that innervate the injection site. In addition to robust expression at the site of injection, ASM mRNA and protein are also detected in several distal regions outside of the ipsilateral (injected) hippocampus, specifically, in the contralateral hippocampal dentate gyrus and CA3, and the medial septum and entorhinal cortex. The invention is further based, in part, on the discovery and demonstration of the extensive correction of lysosomal storage pathology at the distal sites thereby allowing a larger volume of correction via a smaller number of injection sites.

Accordingly, in one aspect, the present invention provides methods for treating neurometabolic disorders in mammals. The populations treated by the methods of the invention include, but are not limited to, patients having or at risk for developing a neurometabolic disorder, e.g., a LSD, such as diseases listed in Table 1, particularly, if such a disease affects the CNS. In an illustrative embodiment, the disease is type A Niemann-Pick disease. In certain embodiments, neurometabolic disorders may exclude Alzheimer's, Parkinson, Huntington, Tay Sachs, Lesch-Nyan, and Creutzfeldt-Jakob diseases. However, methods of the invention utilizing a metalloendopeptidase as a therapeutic transgene, are specifically useful to the treatment of Alzheimer's disease and amyloid-related disorders.

In some embodiments, the method of treating a neurometabolic disorder comprises administration of a high titer AAV vector carrying a therapeutic transgene so that the transgene product is expressed at a therapeutic level in a second site within the CNS distal to the first site. In some embodiments, the viral titer of the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ to/ml); or (c) 5, 6, 7, 8, 8.4, 9, 9.3, 10, 15, 20, 25, or 50 ($\times 10^{10}$ iu/ml). In further embodiments, the administration is accomplished by direct intraparenchymal injection of a high titer AAV vector solution into the diseased brain, thereafter the transgene is expressed distally, contralaterally or ipsilaterally, to the administration site at a therapeutic level at least 2, 3, 5, 8, 10, 15, 20, 25, 30, 35, 40, 45, or 50 mm from the administration site.

The distance between the first and the second sites is defined as the minimal distance region between the site of administration (first site) and the boundary of the detectable transduction of the distal site (second site) as measured using procedures known in the art or as described in the Examples, e.g., in situ hybridization. Some neurons in the CNS of larger mammals may span large distances by virtue of their axonal projections. For example, in humans, some axons may span a distance of 1000 mm or greater. Thus, in various methods of the invention, AAV can be axonally transported along the entire length of the axon at such a distance to reach and transduce the parent cell body.

A site of vector administration within the CNS is chosen based on the desired target region of neuropathology and the topology of brain circuits involved so long as an administration site and the target region have axonal connections. The target region can be defined, for example, using 3-D sterotaxic coordinates. In some embodiments, the administration site is chosen so that at least 0.1, 0.5, 1, 5, or 10% of the total amount of vector injected is delivered distally at the target region of at least 1, 200, 500, or 1000 mm$^3$. An administration site may be localized in a region innervated by projection neurons connecting distal regions of the brain. For example, the substantia nigra and bventral tegmental area send dense projections to the caudate and putamen (collectively known as the striatum). Neurons within the substantia nigra and ventral tegmentum can be targeted for transduction by retrograde transport of AAV following injection into the striatum. As another example, the hippocampus receives well-defined, predictable axonal projections from other regions of the brain. Other administration sites may be localized, for example, in the spinal cord, brainstem (medulla and pons), mesencephalon, cerebellum (including the deep cerebellar nuclei), diencephalon (thalamus, hypothalamus), telencephalon (corpus striatum, cerebral cortex, or, within the cortex, the occipital, temporal, parietal or frontal lobes), or combinations thereof.

For identification of structures in the human brain, see, e.g., The Human Brain: Surface, Three-Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co-Planar Sterotaxic Atlas of the Human Brain: 3-Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000. If desired, the human brain structure can be correlated to similar structures in the brain of another mammal. For example, most mammals, including humans and rodents, show a similar topographical organization of the entorhinal-hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw-Hill, 1991; The Rat Nervous System, 2nd ed., ed. Paxinos, Academic Press, 1995). Furthermore, layer II cells of the entorhinal cortex project to the dentate gyrus, and they terminate in the outer two-thirds of the molecular layer of the dentate gyrus. The axons from layer III cells project bilaterally to the cornu ammonis areas CA1 and CA3 of the hippocampus, terminating in the stratum lacunose molecular layer.

The second (target) site can be located any region of the CNS, including the brain and the spinal cord, that contains a neurons that project to the first (administration) site. In some embodiments, the second site is in a region of the CNS chosen from the substantia nigra, the medulla oblongata, or the spinal cord.

To deliver the vector specifically to a particular region of the central nervous system, especially to a particular region of the brain, it may be administered by sterotaxic microinjection. For example, on the day of surgery, patients will have the sterotaxic frame base fixed in place (screwed into the skull). The brain with sterotaxic frame base (MRI-compatible with fiduciary markings) will be imaged using high resolution MRI. The MRI images will then be transferred to a computer that runs stereotaxic software. A series of coronal, sagittal and axial images will be used to determine the target site of vector injection, and trajectory. The software directly translates the trajectory into 3-dimensional coordinates appropriate for the stereotaxic frame. Burr holes are drilled above the entry site and the stereotaxic apparatus localized with the needle implanted at the given depth. The vector in a pharmaceutically acceptable carrier will then be injected. The AAV vector is then administered by direct injection to the primary target site and retrogradely transported to distal target sites via axons. Additional routes of administration may be used, e.g., superficial cortical application under direct visualization, or other non-sterotaxic application.

The total volume of material to be administered, and the total number of vector particles to be administered, will be determined by those skilled in the art based upon known aspects of gene therapy. Therapeutic effectiveness and safety can be tested in an appropriate animal model. For example, a variety of well-characterized animal models exist for LSDs, e.g., as described herein or in Watson et al. (2001) Methods Mol. Med., 76:383-403; or Jeyakumar et al. (2002) Neuropath. Appl. Neurobiol., 28:343-357.

In experimental mice, the total volume of injected AAV solution is for example, between 1 to 5 µl. For other mammals, including the human brain, volumes and delivery rates are appropriately scaled. For example, it has been demonstrated that volumes of 150 µl can be safely injected in the primate brain (Janson et al. (2002) Hum. Gene Ther., 13:1391-1412). Treatment may consist of a single injection per target site, or may be repeated along the injection tract, if necessary. Multiple injection sites can be used. For example, in some embodiments, in addition to the first administration site, a composition comprising AAV carrying a transgene is administered to another site which can be contralateral or ipsilateral to the first administration site.

In another aspect, the invention provides a method of delivering a recombinant AAV genome via retrograde axonal transport to the nucleus of a disease-compromised neuron in vivo. In some embodiments, the cellular pathology exhibited by a neuron is that of a LSD such as listed in Table 1 (see, e.g., Walkley (1998) Brain Pathol., 8:175-193). In an illustrative embodiment, the disease is Niemann-Pick A disease. The method of delivering a recombinant AAV genome to the nucleus of a disease-compromised neuron comprises contacting an axonal ending of a disease-compromised neuron with a composition comprising an AAV viral particle comprising the recombinant AAV genome and allowing the viral particle to be endocytosed and retrogradely transported intracellulary along the axon to the nucleus of the neuron, wherein the concentration of AAV genomes in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ to/ml); or (c) 5, 6, 7, 8, 8.4, 9, 9.3, 10, 15, 20, 25, or 50 ($\times 10^{10}$ iu/ml). In certain embodiments, the neuron is a projection neuron and/or the distance from the axonal ending to the nucleus of the neuron is at least 2, 3, 5, 8, 10, 15, 20, 25, 30, 35, 40, 45, or 50 mm. In various embodiments, the AAV genome is transported along the entire length of the axon, at distances varying depending on the axon length. In humans, these distances may be as much as 1000 mm or greater.

In another aspect, the invention provides a method of delivering a transgene product to a target cell of the CNS, which is a neuron or a glial cell, in a mammal afflicted with a disorder, for example an LSD as listed in Table 1. The method comprises contacting an axonal ending of a neuron with a composition comprising an AAV vector carrying at least a part of a gene encoding a therapeutic transgene product; allowing the viral particles to be endocytosed and retrogradely transported intracellularly along the axon to the nucleus of the neuron; allowing the transgene product to be expressed and secreted by the neuron; and allowing a second cell to uptake the transgene product, wherein the transgene product thereby alleviates pathology in the second cell. In some embodiments the concentration of the AAV vector in the composition is at least: (a) 5, 6, 7, 8, 8.4, 9, 9.3, 10, 15, 20, 25, or 50 ($\times 10^{12}$ gp/ml); (b) 5, 6, 7, 8, 8.4, 9, 9.3, 10, 15, 20, 25, or 50 ($\times 10^{9}$ tu/ml); or (c) 5, 6, 7, 8, 8.4, 9, 9.3, 10, 15, 20, 25, or 50 ($\times 10^{10}$ iu/ml). For example, lysosomal hydrolases can be secreted by transduced cells and subsequently taken up by another cell via mannose-6-phosphate receptor-mediated endocytosis, the second cell being transduced or non-transduced (Sando et al. (1977) Cell, 12:619-627; Taylor et al. (1997) Nat. Med., 3:771-774; Miranda et al. (2000) Gene Ther., 7:1768-1776; and Jin et al. (2002) J. Clin. Invest., 109:1183-1191).

In the methods of the invention, AAV of any serotype can be used so long as the vector is capable of undergoing retrograde axonal transport in a disease-compromised brain. The serotype of the viral vector used in certain embodiments of the invention is selected from the group consisting from AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV2 genome. (Auricchio et al., (2001) Hum. Mol. Genet., 10(26):3075-81.) However, AAV5 may be specifically excluded from the methods of the invention utilizing a metalloendopeptidase, e.g., neprilysin, as a therapeutic transgene.

AAV vectors are derived from single-stranded (ss) DNA parvoviruses that are nonpathogenic for mammals (reviewed in Muzyscka (1992) Curr. Top. Microb. Immunol., 158:97-129). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV2. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888.

In certain methods of the invention, the vector comprises a transgene operably linked to a promoter. The transgene encodes a biologically active molecule, expression of which in the CNS results in at least partial correction of neuropathology. In some embodiments, the transgene encodes a lysosomal hydrolase. In an illustrative embodiment, the lysosomal hydrolase is ASM. The genomic and functional cDNA sequences of human ASM have been published (see, e.g., U.S. Pat. Nos. 5,773,278 and 6,541,218). Other lysosomal hydrolases can be used for appropriate diseases, for example, as listed in Table 1.

The invention further provides methods of treating Alzheimer's disease in mammals, including humans. In such methods, the transgene encodes a metalloendopeptidase. The metalloendopeptidase can be, for example, the amyloid-beta degrading enzyme neprilysin (EC 3.4.24.11; sequence accession number, e.g., P08473 (SWISS-PROT)), the insulin-degrading enzyme insulysin (EC 3.4.24.56; sequence accession number, e.g., P14735 (SWISS-PROT)), or thimet oligopeptidase (EC 3.4.24.15; sequence accession number, e.g., P52888 (SWISS-PROT)).

The level of transgene expression in eukaryotic cells is largely determined by the transcriptional promoter within the transgene expression cassette. Promoters that show long-term activity and are tissue- and even cell-specific are used in some embodiments. Nonlimiting examples of promoters include, but are not limited to, the cytomegalovirus (CMV) promoter (Kaplitt et al. (1994) Nat. Genet., 8:148-154), CMV/human β3-globin promoter (Mandel et al. (1998) J. Neurosci., 18:4271-4284), GFAP promoter (Xu et al. (2001) Gene Ther., 8:1323-1332), the 1.8-kb neuron-specific enolase (NSE) promoter (Klein et al. (1998) Exp. Neurol., 150:183-194), chicken beta actin (CBA) promoter (Miyazaki (1989) Gene, 79:269-277) and the β-glucuronidase (GUSB) promoter (Shipley et al. (1991) Genetics, 10:1009-1018). To prolong expression, other regulatory elements may additionally be operably linked to the transgene, such as, e.g., the Woodchuck Hepatitis Virus Post-Regulatory Element (WPRE) (Donello et al. (1998) J. Virol., 72, 5085-5092) or the bovine growth hormone (BGH) polyadenylation site.

For some CNS gene therapy applications, it will be necessary to control transcriptional activity. To this end, pharmacological regulation of gene expression with AAV vectors can been obtained by including various regulatory elements and drug-responsive promoters as described, for example, in Habermaet al. (1998) Gene Ther., 5:1604-16011; and Ye et al. (1995) Science, 283:88-91.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Titration of Recombinant Vectors

AAV vector titers were measured according to genome copy number (genome particles per milliliter). Genome particle concentrations were based on Taqman® PCR of the vector DNA as previously reported (Clark et al. (1999) Hum. Gene Ther., 10:1031-1039; Veldwijk et al. (2002) Mol. Ther., 6:272-278). Briefly, purified AAV-ASM was treated with capsid digestion buffer (50 mM Tris-HCl pH 8.0, 1.0 mM EDTA, 0.5% SDS, 1.0 mg/ml proteinase K) at 50° C. for 1 hour to release vector DNA. DNA samples were put through a polymerase chain reaction (PCR) with primers that anneal to specific sequences in the vector DNA, such as the promoter region, transgene, or the poly A sequence. The PCR results were then quantified by a Real-time Taqman® software, such as that provided by the Perkin Elmer-Applied Biosystems (Foster City, Calif.) Prism 7700 Sequence Detector System.

Vectors carrying an assayable marker gene such as the β-galactosidase or green fluorescent protein gene (GFP) can be titered using an infectivity assay. Susceptible cells (e.g., HeLa, or COS cells) are transduced with the AAV and an assay is performed to determine gene expression such as staining of β-galactosidase vector-transduced cells with X-gal (5-bromo-4chloro-3-indolyl-β-D-galactopyranoside) or fluorescence microscopy for GFP-transduced cells. For example, the assay is performed as follows: $4 \times 10^4$ HeLa cells are plated in each well of a 24-well culture plate using normal growth media. After attachment, i.e., about 24 hours later, the cells are infected with Ad type 5 at a multiplicity of infection (MOI) of 10 and transduced with serial dilutions of the packaged vector and incubated at 37° C. One to three days later, before extensive cytopathic effects are observed, the appropriate assay is performed on the cells (e.g., X-gal staining or fluorescence microscopy). If a reporter gene such as β-galactosidase is used, the cells are fixed in 2% paraformaldehyde, 0.5% glutaraldehyde and stained for β-galactosidase activity using X-gal. Vector dilutions that give well-separated cells are counted. Each positive cell represents 1 transduction unit (tu) of vector.

Correction of LSD Pathology in the Mouse Brain

Ten-week old ASMKO mice contain significant NPD pathology in the central nervous system. Identification of homozygous recessive mutants was verified by PCR. Sixteen 10-week old ASMKO mice were anesthetized with isoflurane and mounted on a stereotaxic frame, an incision was made to expose the underlying skull, and a single drill hole was made over one hemisphere of each mouse. Two microliters of high titer ($9.3 \times 10^{12}$ gp/ml) AAV2-CMV-ASM (Targeted Genetics, Seattle, Wash.) were injected into the hippocampus at a final stereotaxic coordinate of 2.0 mm rostral of bregma, 1.5 mm right of midline, and 2.0 mm ventral to pial surface. This hippocampal coordinates ensured that the AAV2 vector was exposed to neurons of the dentate gyrus and of the cornu ammonis area 3 (CA3), as well as to axonal endings of projection neurons of the contralateral hippocampus, medial septum and entorhinal cortex. The injections were performed at a rate of 0.2 μl/minute, and a total of $1.86 \times 10^{10}$ genomic particles were administered into each brain. The mice were then sacrificed at either 5 (n=8) or 15 (n=8) weeks post injection (pi). Eight brains (n=4 each at 5 and 15 weeks pi) were analyzed for ASM mRNA and protein distribution, and for the reduction of the supraphysiologic levels of cholesterol in the lysosomes. The remaining 8 brains (n=4 each at 5 and 15 weeks pi) were processed for histopathology to analyze the correction of accumulated and distended lysosomes, which is the most direct and accurate method for determining reversal of storage pathology for LSDs.

Robust transduction was detected in the injected (ipsilateral) hippocampus at 5 and 15 weeks pi. The granule cell layer and hilus of the dentate gyrus, and the pyramidal and oriens cell layers of CA3 were extensively transduced by the AAV2 vector. This impressive pattern of transduction extended to other regions of the ipsilateral hippocampus, such as the subiculum and cornu ammonis area 1 (CA1) and 2 (CA2). Immunofluorescence with an anti-human ASM monoclonal antibody confirmed the presence of ASM protein in many cells. The overall protein pattern was similar to the mRNA pattern, with some additional localized spread of protein.

Figure 1A:
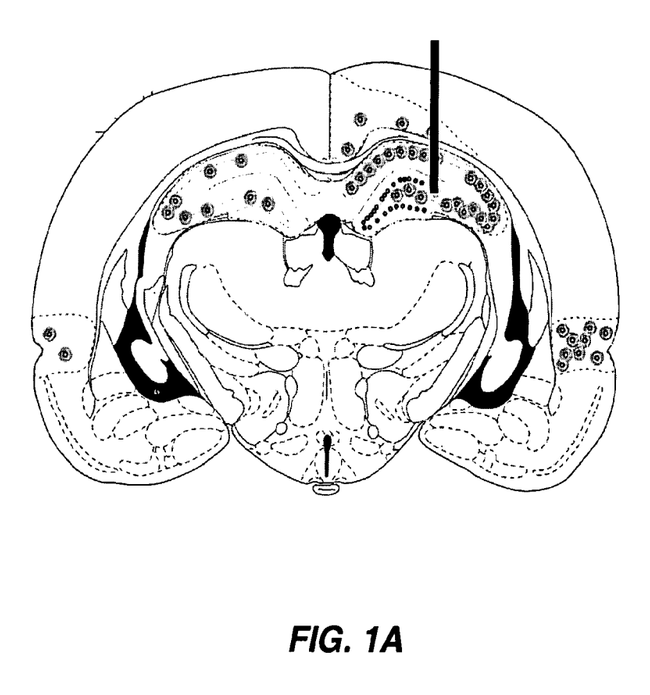
FIG. 1A depicts a representation of a cross-section of the ASMKO mouse brain, at 5 or 15 weeks following a 2 μl injection of high titer (9.3×10$^{12}$ gp/ml) AAV-ASM into the hippocampus. The site of injection is shown by a vertical line; ASM mRNA expression, as detected by in situ hybridization, is represented the smaller circles; and ASM protein expression, as detected by immunohistochemical staining, is represented by the larger shaded circles. The expression pattern resulted in an extensive area of reversal of pathology (represented by the light shading) in the hippocampus and cortical regions in both hemispheres of the brain.
Figure 1B:
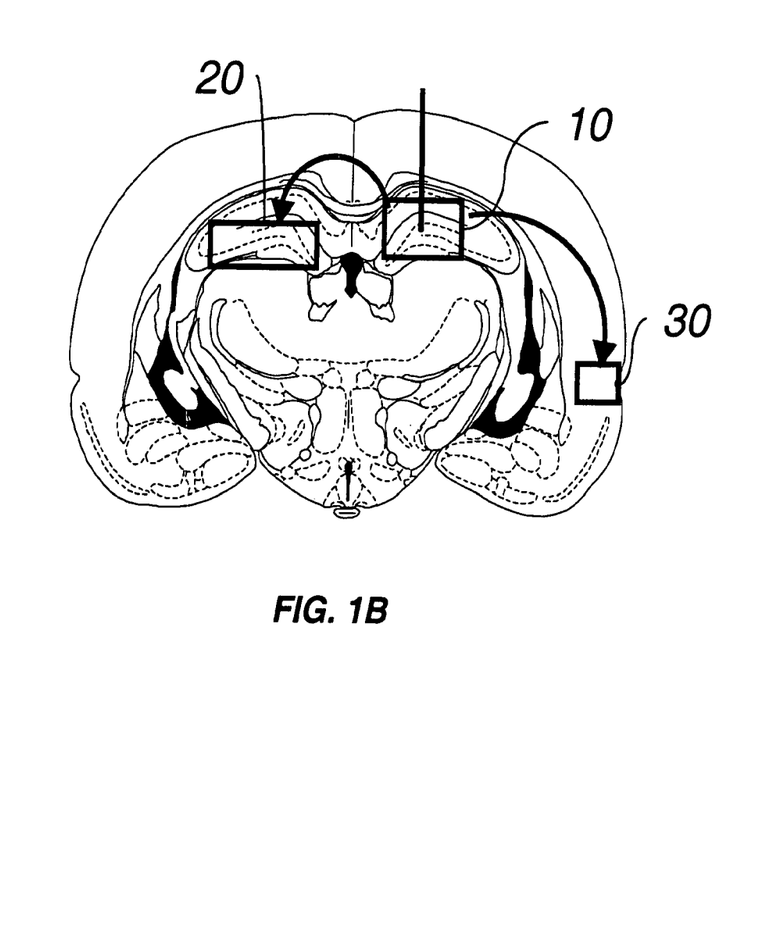
FIG. 1B depicts the axonal transport of AAV to distal regions of the mouse brain following a high titer AAV injection into the hippocampus as described for FIG. 1A. Injection into the hippocampus (10) resulted in axonal transport of the viral vector via the intrahippocampal circuit to the contralateral hippocampus (20) and via the entorhinodentate circuit to the entorhinal cortex (30). The site of injection is shown by a vertical line.
Figure 1C:
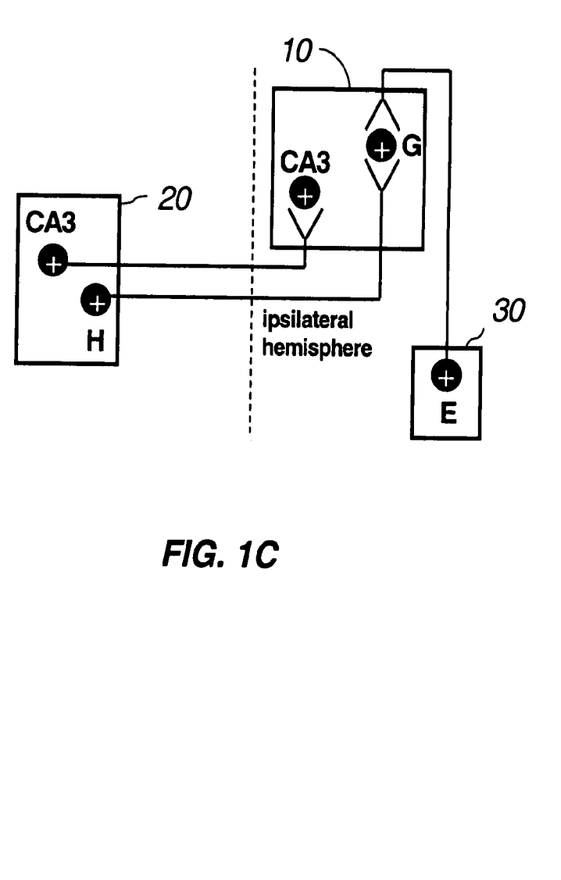
Figure 2A:
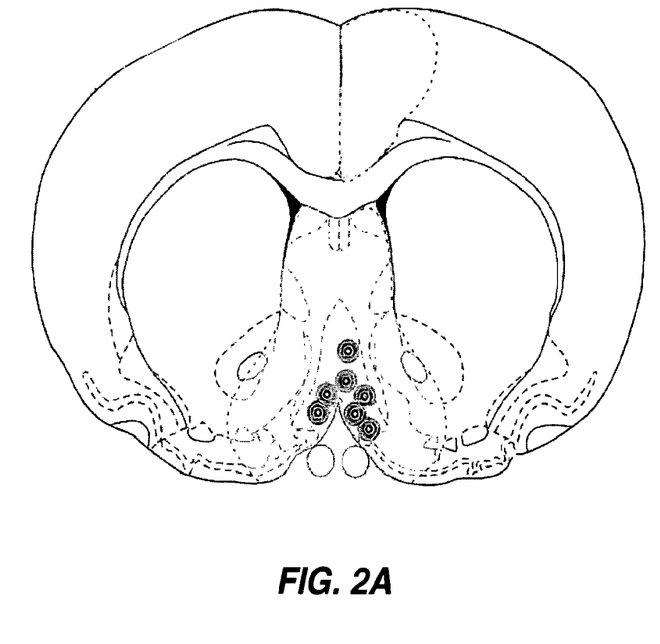
FIG. 2A depicts a representation of a cross-section of the ASMKO mouse brain, at 5 or 15 weeks following an intrahippocampal injection of high titer AAV-ASM as described in FIG. 1A. ASM mRNA expression, as detected by in situ hybridization, is represented by the smaller circles; and ASM protein expression, as detected by immunohistochemical staining, is represented by the larger shaded circles. The injection resulted in ASM mRNA and protein to be detected in the septum. This expression pattern resulted in an extensive area of reversal of pathology (represented by the light shading).
Figure 2B:
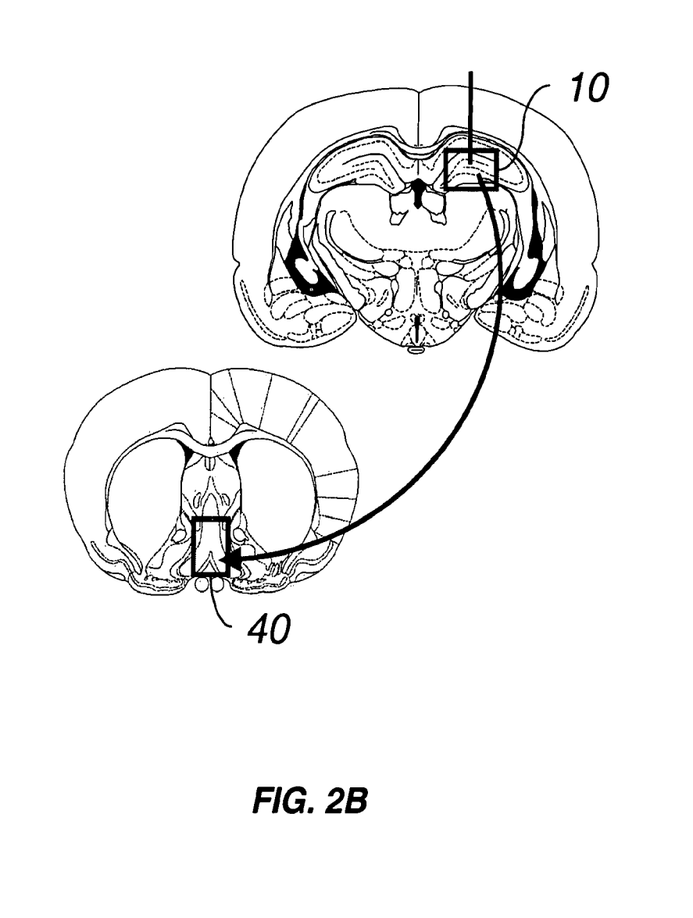
FIG. 2B depicts the axonal transport of AAV to distal regions of the mouse brain, following a high titer injection into the hippocampus as described in FIG. 1A. Injection into the hippocampus (10) resulted in axonal transport of the viral vector via the septohippocampal circuit from the injection site (represented by a vertical line) to the septum (40).
Figure 2C:
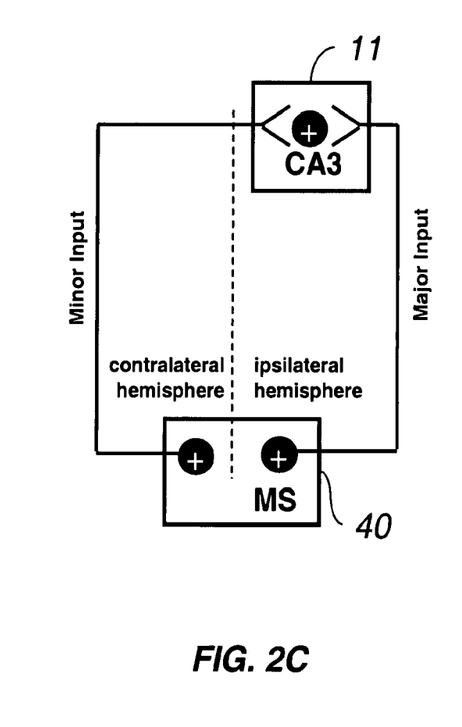

Human ASM mRNA and protein were also detected in regions outside of the ipsilateral hippocampus at both time points. The contralateral dentate gyrus and CA3, and the medial septum and entorhinal cortex were positive for in situ hybridization and immunofluorescence (FIGS. 1A and 2A). The pattern of transduction at these distal sites was consistent with the topographical organization of the projection neurons that innervate the injection site (FIGS. 1B and 2B). This demonstrated that AAV2 underwent retrograde axonal transport in the intrahippocampal, septohippocampal and entorhinodentate circuits of ASMKO brains, and that the viral vector was targeted to the nucleus following transport up the axons (FIGS. 1C and 2C). The pattern of transduction does not support parenchymal diffusion as the reason for AAV2 transport to these distal sites. If such diffusion had occurred, structures between the injected and distal sites would have been exposed to migrating virus. But these intermediate structures were negative for in situ hybridization. For example the striatum, which possesses a strong natural tropism for AAV2, was negative for gene transfer despite being in the direct path between the hippocampus and medial septum. Thus, gene transfer to the distal sites must have arisen by retrograde axonal transport, which indicates that an affected projection neuron can function as an effective highway transport system for AAV2 movement through a diseased brain.

The ability of ASM to reverse the cholesterol abnormalities in the ASMKO brain additionally was investigated. Filipin is an autofluorescent molecule isolated from *Streptomyces filipinensis* that binds to cholesterol complexes (Leventhal et al. (2001) J. Biol. Chem., 276:44976-44983; and Sarna et al. (2001) Eur. J. Neurosci., 13:1-9). Uninjected ASMKO brains had high levels of filipin staining due to these abundant cholesterol complexes, whereas normal mouse brains produced no filipin staining.

Injection of AAV2-CMV-ASM resulted in the complete loss of filipin staining throughout the entire ipsilateral and contralateral hippocampus, septum and entorhinal cortex at 5 and 15 weeks pi of ASMKO mice (FIGS. 1A and 2A). This was in stark contrast to uninjected age-matched ASMKO controls, where high levels of filipin staining were detected in these same structures. The loss of filipin staining in AAV2-injected brains demonstrates that a secondary cellular phenotype (e.g. metabolic defect) of ASM disease was corrected. This strongly suggests that ASM protein was targeted to the lysosome and interacted with the sphingomyelin-cholesterol complex. This interaction likely resulted in the release of cholesterol from sphingomyelin, and subsequent entry of cholesterol into its normal biological pathways (such as degradation or translocation to the plasma membrane (Leventhal et al. (2001) J. Biol. Chem., 276: 44976-44983)).

The loss of filipin staining was observed in all cell layers and subfields of the intrahippocampal, septohippocampal and entorhinodentate circuits. The area of cholesterol correction was far greater and more extensive than the ASM protein pattern. This indicates that, following retrograde axonal transport of AAV2, projection neurons may have functioned as "enzyme pumps" and secreted ASM protein into the surrounding tissue. Significantly, only a small amount of ASM is needed to have a therapeutic effect on cholesterol accumulation within ASMKO-affected cells, an amount below the detection limit of the immunofluorescent protocol.

Whether axonal transport of the AAV2-ASM vector results in the correction of the primary cellular phenotype of NPD also was evaluated. One-micron-thick histopathology brain sections demonstrated a remarkable reduction of accumulated and distended lysosomal pathology in AAV2-CMV-ASM-injected brains at 5 weeks pi (Table 2). Reversal of pathology resulting in partial or complete restoration of normal cellular architecture occurred in all regions of the ipsilateral and the contralateral hemispheres of the hippocampus. The medial septum and the entorhinal cortex also showed a substantial reduction in storage lesions. Similar to the filipin data, the number of cells corrected was greater and more widespread than the ASM protein pattern. Reversal of pathology was evident within regions known to project to the hippocampus including the intrahippocampal, septohippocampal and entorhinodentate circuits. Overall, the volume of correction was 30-35 mm³ or more in the contralateral hippocampus, 5-8 mm³ or more in the ipsilateral entorhinal cortex, 1-2 mm³ or more in the contralateral entorhinal cortex, and 2-3 mm³ or more in the medial septum. This further supports that axonal transport of the viral vector was responsible for this therapeutic effect, because nearby structures (that do not contribute to these circuits) would have been corrected if viral distribution was mediated merely by diffusion (see, "ipsilateral striatum" and "contralateral striatum" in Table 2).

To demonstrate that reversal of pathology was specific to ASM, an additional group of ASMKO mice was injected with a control vector carrying a reporter gene, AAV2-CMV-8-gal (n=2 each at 5 and 15 weeks pi), and processed for histopathology. In all four brains, cells remained inundated with distended lysosomes, and contained other abnormalities such as cytoplasmic swelling and disorganized cellular layers.

TABLE 2

| Brain Region | Untreated | AAV2-ASM Treated |
|---|---|---|
| Ipsilateral Hippocampus | | |
| CA1 Field | ++++ | + |
| CA3 Field | ++++ | + |
| Dentate Granule Cell Layer | ++++ | + |
| Hilus | ++++ | + |
| Contralateral Hippocampus | | |
| CA1 Field | ++++ | + |
| CA3 Field | ++++ | + |
| Dentate Granule Cell Layer | ++++ | + |
| Hilus | ++++ | + |
| Ipsilateral Entorhinal Cortex | ++++ | ++ |
| Contralateral Entorhinal Cortex | ++++ | +++ |
| Ipsilateral Medial Septum | ++++ | ++ |
| Contralateral Medial Septum | ++++ | ++ |
| Ipsilateral Striatum | ++++ | ++++ |
| Contralateral Striatum | ++++ | ++++ |

Figure 3:
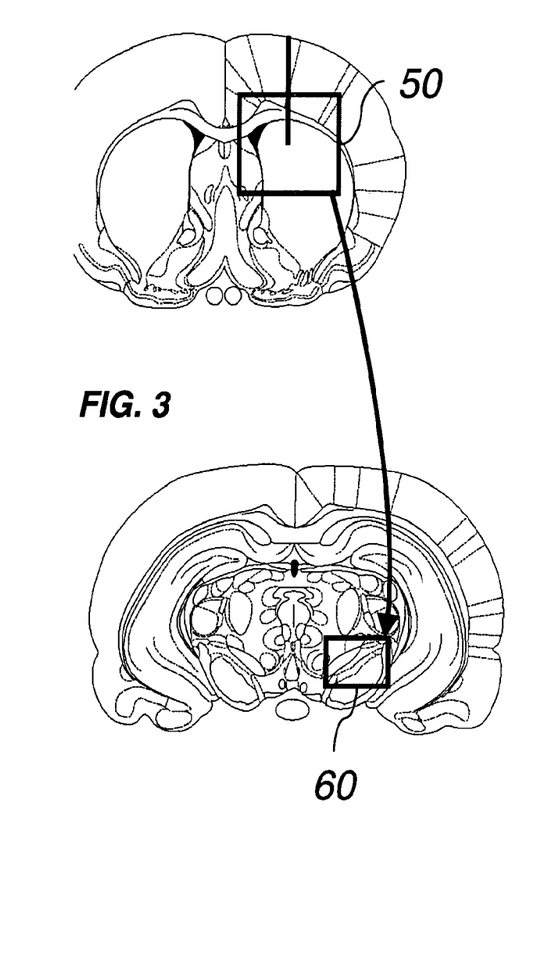
FIG. 3 depicts the axonal transport of AAV in the nigrostriatal circuit, following a high titer injection of AAV into the striatum (50) of the mouse brain. Axonal transport of AAV occurs from the injection site (represented by a vertical line) to the substantia nigra (60).
Figure 4:
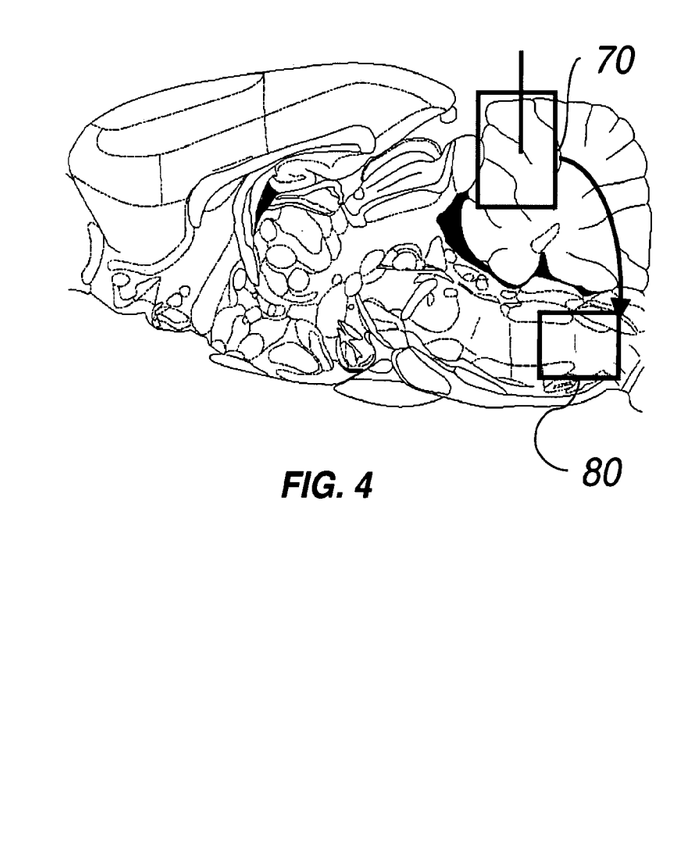
FIG. 4 depicts the axonal transport of AAV in the medullocerebellar circuit, following a high titer injection of AAV-ASM into the cerebellum (70) of the ASMKO mouse brain. Axonal transport of AAV2 occurs from the injection site (represented by a vertical line) to the medulla oblongata (80).

++++ high level of pathology in virtually all cells
+++ pathology in many cells, correction is observed in some cells
++ pathology in some cells, correction is observed in many cells
+ little or no pathology is in most cells, virtually every cell is corrected Thus, in accordance with the present invention, a single injection of high titer AAV2 vector is sufficient to transfer the ASM gene to structures that innervate the ASMKO affected hippocampus. The number of structures positive for AAV2 vector was greater than that demonstrated by a recent study in the normal rat hippocampus, which showed axonal transport only in the entorhinodentate circuit (Kaspar et al. (2002) Mol. Ther., 5:50-56). The results described herein demonstrate that axonal transport can occur in projection neurons inflicted with storage pathology, and that this mode of transport results in the clearance of storage pathology in proximal structures and multiple regions distal to the injection site. We also demonstrate that axonal transport is not limited to only those circuits associated with the hippocampus. Retrograde axonal transport occurred in the nigrostriatal (FIG. 3) and in the medullocerebellar (FIG. 4) circuits. This demonstrates that axonal transport of AAV2 in diseased-compromised neurons is a general property of the viral vector.

Figure 5:
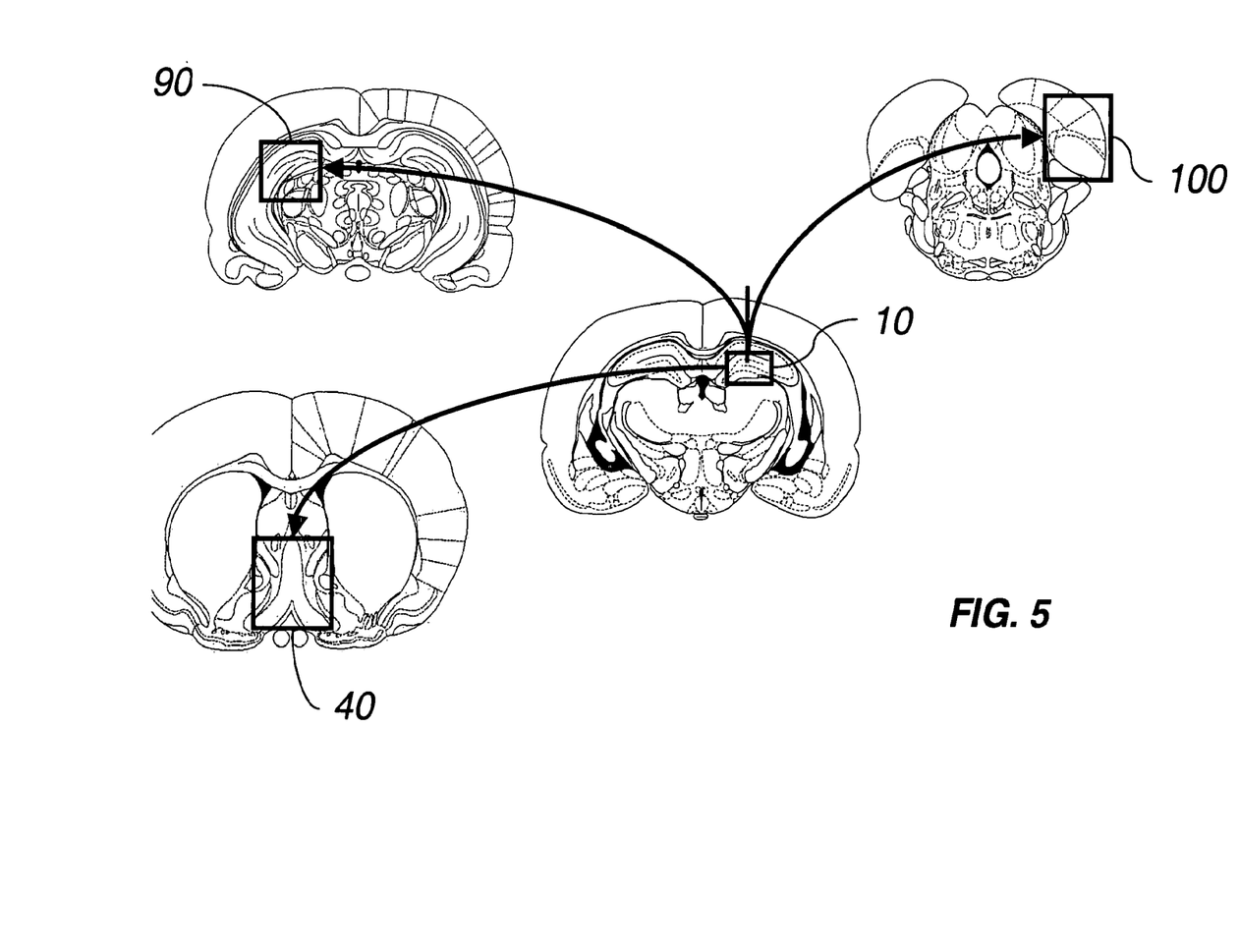
FIG. 5 depicts axonal transport of AAV in the intrahippocampal, nigrostriatal, and entorhinodentate circuits following high-titer injection of AAV7-ASM in the ipsilateral hippocampus (10). Transduced cells were detected, as determined by in situ hybridization, along the entire rostral-caudal axis of the contralateral hippocampus (90), medial septum (40), and entorhinal cortex (100) after AAV7-ASM injection of the ipsilateral hippocampus (represented by a vertical line).

A similar study was performed with AAV1-ASM at the concentrations of $1-4 \times 10^{13}$ gp/ml and AAV7-ASM at the concentration of $8.4 \times 10^{12}$ gp/ml. While AAV1 did not exhibit detectable retrograde axonal transport, AAV7 did undergo retrograde axonal transport, similar to AAV2, and produced correction of LSD pathology in distal regions (see FIG. 5).

Injection of AAV Into the Cerebellum

ASMKO mice were anesthetized with isoflurane and mounted on a stereotaxic frame. Bregma was located as a reference point to determine the drilling location for injection into the deep cerebellar nuclei region of the cerebellum. Once located, an incision was made to expose the underlying skull, and a single drill hole was made into the skull without piercing the brain surface. A Hamilton syringe was lowered into the brain via the hole and AAV2-CMV-ASM was injected into the deep cerebellar nuclei at a rate of 0.5 microliters per second. Three microliters were injected for a total dose of $1 \times 10^{10}$ genome particles. Mice were sacrificed 7 weeks post injection. The brains and spinal cords were evaluated for ASM mRNA expression, ASM protein expression, filipin staining, and calbindin staining.

Filipin is an autofluorescent molecule that binds to cholesterol complexes. Untreated ASMKO mice have high levels of filipin staining due to abundant cholesterol complexes, which accumulate as a result of their disease. In contrast, normal mouse brains do not exhibit filipin staining.

Calbindin is a marker of Purkinje cells, which are found in the cerebellum and are involved in coordinated movements. In the ASMKO mouse, Purkinje cells die off in these mice as they age, resulting in decreased coordinated movement behavior. This loss of Purkinje cells and the correlative loss of coordinated movement behavior are not observed in normal mice.

Following AAV2 injection into the deep cerebellar nucleus, the cerebellum was positive for ASM mRNA, ASM protein, and calbindin staining. These results demonstrate that ability of AAV2 to transduce the cerebellum following injection into the deep cerebellar nuclei. Moreover, the cerebellar transduction and resulting ASM expression prevented Purkinje cell death as evidenced by the presence of calbindin staining in the treated mice. In AAV-ASM treated mice, expression of hASM protein was also observed throughout the brainstem, thalamus, and mescencephalon. hASM protein expression in these regions overlapped with regional clearance of filipin/cholesterol staining. Overall, in the cerebellum there was a positive relationship between ASM protein levels, filipin clearance, and Purkinje cell survival.

ASM mRNA and ASM protein were also detected outside the cerebellum. Specifically, the spinal cord was positive for ASM mRNA expression as evidenced by in situ hybridization. The spinal cord was also positive for ASM protein as evidenced by ASM-specific immunofluorescence. These results indicate that the spinal cord was transduced following a distal injection of the AAV vector into the deep cerebellar nuclei. This pattern of transduction was consistent with the topographical organization of the projection neurons that innervate the deep cerebellar nuclei region. These results indicate that the AAV2 vector was taken up by distal spinal cord cells and expressed.

Treatment of Alzheimer's Disease

Alzheimer's disease (AD) is a neurodegenerative disorder characterized by the accumulation of amyloid β-peptide (Aβ) due to decreased Aβ catabolism. As Aβ accumulates, it aggregates into extracellular plaques, causing impairment of synaptic function and loss of neurons. The pathology leads to dementia, loss of coordination, and death.

Neprilysin is a 97 kD membrane-bound zinc metalloendopeptidase that is the rate-limiting enzyme in the normal degradation of Aβ. Introduction of neprilysin may decelerate the progression of the disease by removing Aβ pools before aggregation. Indeed, neprilysin was shown to degrade oligomeric forms of Aβ thereby removing existing plaques in an animal model of AD (Kanemitsu et al. (2003) Neurosci. Lett., 350:113-116). Neprilysin knockout mice exhibit high levels of Aβ (Iwata et al. (2001) J. Neurosci., 24:991-998). Neprilysin inhibitors, such as thiorphan and phosphoramidon, increase Aβ levels in mouse brain (Iwata et al. (2000)

Nat. Med., 6:143-150). Additionally, decreased neprilysin mRNA levels were found in areas of high amyloid plaque burden in human brains, further demonstrating the link between neprilysin and AD (Yasojima et al. (2001) Neurosci. Lett., 297:97-100).

The areas of brain most affected by AD are the hippocampus, cortex, cerebellum, striatum and thalamus (see, e.g., Iwata et al. (2001) supra; Yasojima et al. (2001) supra). These are the same areas of the brain that show efficient retrograde axonal transport with AAV.

Accordingly, AAV can used to deliver therapeutic transgenes to regions of high plaque burden by direct injection and subsequent translocation of virus through brain circuits to our target sites. Viral vector-mediated gene transfer of neprilysin was effective in treating mouse models of AD (Marr et al. (2003) J. Neurosci., 23:1992-1996; Marr et al. (2004) J. Mol. Neurosci., 22:5-11; Iwata et al. (2004) J. Neurosci., 24:991-998). A recent report showed that AAV5-neprilysin removed Aβ from the pre-synaptic terminals of the hippocampus in neprilysin-deficient mice, decelerating plaque formation at the synapses (Iwata et al. (2004) supra). In this report, neprilsyin was found in the contralateral hippocampus but whether this is attributable to retrograde transport of virus or anterograde transport of expressed protein remains unknown.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating Niemann-Pick A disease or Niemann-Pick B disease in a mammalian subject, said method comprising:
   directly, administering at least $1.86 \times 10^{10}$ gp of a recombinant adeno-associated virus-2 (AAV-2) vector comprising a nucleic acid sequence encoding acid sphingomyelinase (ASM) operably linked to a promoter, to a first administration site in the hippocampus of the mammalian subject; and inhibiting cholesterol accumulation of the Niemann-Pick A disease or Niemann-Pick B disease in a distal target site by expressing ASM protein at the distal target site via the AAV-2 vector undergoing retrograde axonal transport to the distal target site and transducing cells located at the distal target site, wherein the distal target site is contralateral to the first administration site,
   wherein the distance between the first administration site and the distal target site is at least 5 mm, wherein the first administration site and the distal target site have axonal connections, and
   wherein the distal target site is in the dentate gyrus, cornu ammonis area 3 (CA3) or entorhinal cortex.

2. The method of claim 1, wherein the mammalian subject is human.

3. A method of treating Niemann-Pick A disease or Niemann-Pick B disease in a mammalian subject, the method comprising:
   directly, administering at least $5 \times 10^{12}$ gp/ml of a recombinant AAV-2 vector comprising a nucleic acid sequence encoding acid sphingomyelinase (ASM) operably linked to a promoter, to a first administration site in the hippocampus of the mammalian subject; and inhibiting cholesterol accumulation of the Niemann-Pick A disease or Niemann-Pick B disease in a distal target site by expressing ASM protein at the distal target site via the AAV-2 vector undergoing retrograde axonal transport to the distal target site and transducing cells located at the distal target site,
   wherein the distal target site is contralateral to the first administration site, wherein the distance between the first administration site and the distal target site is at least 5 mm,
   wherein the first administration site and the distal target site have axonal connections, and
   wherein the distal target site is in the dentate gyrus, cornu ammonis area 3 (CA3), or entorhinal cortex.

4. The method of claim 3, wherein the mammalian subject is human.

* * * * *